United States Patent
Glover (10) Patent No.: US 7,462,835 B2
(45) Date of Patent: Dec. 9, 2008

(54) UV TRANSMITTANCE MEASURING DEVICE

(75) Inventor: James Andrew Glover, Whitby (GB)

(73) Assignee: Ontario Ltd, Whitby (CA)

( * ) Notice: Subject to any disclaimer, the term of this patent is extended or adjusted under 35 U.S.C. 154(b) by 0 days.

(21) Appl. No.: 11/455,933

(22) Filed: Jun. 20, 2006

(65) Prior Publication Data

US 2007/0023670 A1    Feb. 1, 2007

Related U.S. Application Data

(60) Provisional application No. 60/691,803, filed on Jun. 20, 2005.

(51) Int. Cl.
*G01N 21/33*    (2006.01)

(52) U.S. Cl. ...................................... 250/373

(58) Field of Classification Search .................. 250/373
See application file for complete search history.

(56) References Cited

U.S. PATENT DOCUMENTS

| | | | | |
|---|---|---|---|---|
| 3,553,454 | A * | 1/1971 | Olson et al. ................. | 250/328 |
| 3,579,105 | A | 5/1971 | Scott | |
| 3,591,801 | A * | 7/1971 | Watson ....................... | 250/373 |
| 4,011,451 | A * | 3/1977 | Nelson ........................ | 250/343 |
| 4,021,670 | A * | 5/1977 | Noakes ....................... | 250/328 |
| 4,029,958 | A * | 6/1977 | Wright ................... | 250/223 B |
| 4,276,475 | A * | 6/1981 | Nelson ........................ | 250/373 |
| 4,290,695 | A | 9/1981 | Schmitt | |
| 4,577,106 | A | 3/1986 | Fukasawa et al. | |
| 4,775,794 | A * | 10/1988 | Behmann ..................... | 250/373 |
| 4,832,491 | A | 5/1989 | Sharpe et al. | |
| 5,021,196 | A * | 6/1991 | Crano et al. ................. | 252/586 |
| 5,712,703 | A * | 1/1998 | Ando et al. .................. | 356/319 |
| 6,365,906 | B1 * | 4/2002 | Spangenberg et al. ..... | 250/559.3 |
| 6,831,740 | B2 | 12/2004 | Herzinger et al. ........... | 356/319 |
| 2002/0066874 | A1 * | 6/2002 | Drescher ................. | 250/504 R |

* cited by examiner

*Primary Examiner*—David P. Porta
*Assistant Examiner*—Kiho Kim
(74) *Attorney, Agent, or Firm*—Lynn C. Schumacher; Hill & Schumacher (57) ABSTRACT

A device to measure the amount of ultraviolet (UV) light transmitted through a water sample, relative to the amount of UV light transmitted through a sample of known UV transmittance, known as UV percent transmittance (UVT). A single UV sensor is used to measure the amount of UV light transmitted through the blank sample and through the water sample under test. In order to maintain accuracy, compensation must be made for fluctuations or drift in the UV lamp output which is common in UV lamps and due primarily to changes in temperature and imperfections in the lamp. The UV sensor measures the amount of light being emitted by the lamp at the times before and/or after the UV sensor measures the amount of UV light transmitted through the blank and water samples. A microprocessor computes the UVT while using the detector readings to compensate the calculated UVT for any drift and fluctuations in the UV lamp output.

29 Claims, 2 Drawing Sheets

UV TRANSMITTANCE MEASURING DEVICE

CROSS REFERENCE TO RELATED U.S. PATENT APPLICATIONS

This patent application relates to U.S. utility patent application Ser. No. 60/691,803 filed on Jun. 20, 2005, entitled UV TRANSMITTANCE MEASURING DEVICE, filed in English, which is incorporated herein in its entirety by reference.

FIELD OF THE INVENTION

The present invention is related to an apparatus for measuring water quality and particularly relates to several applications within the water and wastewater treatment industry.

BACKGROUND OF THE INVENTION

Rapid and reliable measurement of water quality is of major importance, particularly with respect to drinking water. Ultraviolet transmittance (UVT) is a measure of the transmittance of water to UV light. Fundamentally, this requires a UV light source to shine UV light through a water sample and into a UV detector. The UVT of a water sample is calculated as the amount of UV light that passes through the water sample under test (test sample) divided by the amount of light that passes through a water sample of known UVT (blank sample), preferably of 100% UVT. There are a number of existing products that make use of this method to measure UVT.

This method, often called the "single-beam" method, is well known in the art and has long been used in photometric instruments of various and multiple wavelengths. U.S. Pat. No. 4,832,491 describes the use of this method whereby the ratio described above is determined for each selected wavelength to enable the calculation of an absorbance spectrum of the sample.

One of the main difficulties when designing UVT instrumentation is due to the nature of UV light sources. The most common UV light source is the mercury lamp, which has a tendency to drift and fluctuate causing significant errors in the UVT measurements when using the single-beam method described above. Such fluctuation and drift is very common in UV lamps and is due primarily to changes in temperature and imperfections in the ballast and lamp.

Some low cost designs make no attempt to compensate for such fluctuations and drift which severely reduces accuracy. These designs require the user to wait up to 30 minutes after turning on the instrument to allow as much time for the lamp to stabilize as possible. However, significant errors are still common.

One way to reduce these errors is to use a feedback loop to allow the instrument to adjust the lamp output in an attempt to maintain a constant output. However, this is very costly to implement since additional electronics, a second sensor and a proportionally adjustable ballast is required to power the UV lamp.

Another way to attempt to reduce these errors is to use a second beam of light. This method is commonly called the "double-beam" method and is well known in the art and has long been used in photometric instruments of various and multiple wavelengths.

There are several different implementations of double-beam technology. One such implementation is to use a light source with two chambers and two light sensors in which one chamber is intended to accept a test sample and the other chamber is intended to accept a blank sample. A ratio of the output from each light sensor is used to determine the transmittance or absorbance of the sample under test. Since the first and second light sensors output the blank sample and test sample data at the same time, errors caused by lamp output drift and fluctuations are eliminated. However, this method introduces new errors due to the use of two sensors. Differences in the optics of each sensor location can produce non-linear differences between the measurements made using each sensor. Differences in the electronic signal path of each UV sensor can also significantly affect the measurements of each sensor. Also, if each sensor is looking at a different part of the lamp and/or looking at the lamp from a different angle, errors can occur since the UV lamp output varies not only over time, but also over the surface of the lamp. For these reasons, this particular design is not very common.

Another double-beam method uses only one light sensor so that the errors introduced with a second sensor are eliminated. A sample chamber and a reference chamber are still used, but instead of two light beams propagating through the two chambers to two sensors, one light beam is switched intermittently between the two chambers using a switchable beam splitting apparatus, where the light beam from one chamber at a time is incident on a single light sensor. U.S. Pat. No. 4,577,106 describes the use of this design using one light detector and a mirror capable of rotating with the purpose of directing the light beam through either sample or reference chambers at certain times.

However, there are still errors present in this method that are not present in the single-beam method. Since two sample vials are required, one for the test sample and one for the blank sample, significant errors can occur since the two sample vials are not necessarily matched. Also, this system is expensive due to use of a switchable beam splitting apparatus and the potential use of precision manufacturing to attempt to match the optics of the two beam paths. It should also be noted that the cost of such optical apparatus becomes especially expensive when using UV light since UV light does not readily transmit through glass lenses making the use a quartz optical components necessary. UV light also has a tendency to erode reflective surfaces, making the use of mirrors undesirable.

Yet another double-beam method is available. This method again uses two signal paths through two chambers. However, instead of inserting the water sample under test in one chamber and the reference sample in the second chamber, this method uses the first chamber for both the water sample under test and the reference sample, at alternate times, and the second chamber is left empty such that the light is allowed to pass freely to the light sensor to provide information on the amount of light output from the lamp at certain times. As before, the transmittance or absorbance is calculated using a ratio of the light transmitted through the test sample to the light transmitted through the blank sample, the same as the single-beam method and the other double beam methods.

However, the second light beam allows the light detector to determine the raw lamp output at the times when the light transmitted through the blank sample and the test sample were determined. This allows the instrument to compensate for lamp drift and fluctuations that occur over that time. U.S. Pat. No. 3,579,105 describes the use of this design using two light detectors. However, this method is still susceptible to errors caused by using the two separate light paths and light detectors, as discussed above.

Therefore, there is a need for a water quality measuring device which is compact, inexpensive and easy to use which avoids the aforementioned limitations. The present invention provides a device that measures the UVT/UVA of water samples while compensating for lamp drift and fluctuations, using only one light detector, one light beam, and without the need for expensive optical components such as UV resistant mirrors and/or quartz lenses.

SUMMARY OF INVENTION

The present invention provides a small, compact device that efficiently and accurately measures, computes and displays the ultraviolet transmittance/ultraviolet absorbance (UVT/UVA) of water samples. The device disclosed herein is used to measure the UVT/UVA of water samples while compensating for lamp drift and fluctuations, using only one light detector, and without the need for expensive optical components such as mirrors and/or quartz lenses.

The present invention is invaluable for companies that design, sell and/or service UV water and wastewater disinfection systems. Since natural organic matter (NOM) in water has strong absorption properties to UV light at the 254 nm wavelength, the invention has many applications in the water and wastewater industry which require the measurement of NOM. Such applications include filtration, coagulation, chlorination, ozone and ion exchange treatment methods, as well as water and wastewater treatment plant efficiency and effectiveness.

The device disclosed herein can also help predict the potential formation of disinfection by-products (DBP's) formed by the reaction of chlorine and dissolved organics within a water or wastewater treatment system. This relates to the determination of the Specific UV Absorbance (SUVA) of a water sample, designated by the Environmental Protection Agency (EPA) as an important water quality parameter.

Thus, the present invention provides an apparatus for measuring the transmittance of ultraviolet radiation through a liquid sample, comprising:

a sample vial holder for holding a sample vial, the sample vial holder defining a path therethrough for transmitting UV light through said sample vial holder;

an ultraviolet lamp for emitting ultraviolet radiation positioned on one side of said sample vial holder for illuminating said vial holder;

at least one sensor for sensing a presence or absence of said sample vial in said vial holder;

a light detector located on the other side of said sample vial holder for detecting an intensity of ultraviolet radiation transmitted through said sample vial holder;

a microprocessor connected to said ultraviolet lamp and said light detector and said at least one sensor, said microprocessor including processing means for processing ultraviolet light intensity signals received from said light detector, said microprocessor including processing means for a) performing a calibration procedure by the steps of:
  i) calculating a first ultraviolet light intensity of ultraviolet light emitted from the ultraviolet lamp without the sample vial located in said vial holder,
  ii) calculating a second ultraviolet light intensity of ultraviolet light transmitted through said sample vial upon insertion of said sample vial into said sample vial holder with a calibrator material located in said sample vial having a known ultraviolet transmittance, and calculating a first ratio of the first and second ultraviolet light intensities;
b) measuring ultraviolet light transmittance of a test liquid sample by the steps of:
  i) calculating a third ultraviolet light intensity of ultraviolet light emitted from the ultraviolet lamp without the sample vial located in said vial holder,
  ii) calculating a fourth ultraviolet light intensity of ultraviolet light emitted from said sample vial upon insertion of said sample vial into said sample vial holder containing a test liquid sample being tested in a liquid quality measurement procedure, and calculating a second ratio of the third and fourth ultraviolet light intensities, and
c) calculating a third ratio of said first and second ratios to determine an ultraviolet transmittance (UVT) of the liquid test sample.

The microprocessor may be programmed to prompt a user to insert the sample vial into the sample vial holder a predetermined time after an initiation of step a) i), and a predetermined time after an initiation of step b) i).

The microprocessor may be programmed to process the ultraviolet light intensity signals received directly from the light detector during step a) i) or b) I) for a pre-selected period of time prior to insertion of the sample vial, and the microprocessor may be programmed to process the ultraviolet light intensity signals received from the sample vial located in the sample vial holder during step a) ii) or b) ii) for a pre-selected period of time after insertion of the sample vial into the sample vial holder.

Alternatively, the microprocessor may be programmed to process the ultraviolet light intensity signals received directly from said light detector during step a) i) or b) i) for a preselected period of time after removal of the sample vial from the sample vial holder, and the microprocessor may be programmed to process the ultraviolet light intensity signals received from the sample vial located in the sample vial holder during step a) ii) or b) ii) for a pre-selected period of time prior to removal of the sample vial from the sample vial holder.

The apparatus may include a second light detector connected to said microprocessor for measuring a direct output of said UV lamp, and wherein said microprocessor is programmed to correct for fluctuations in the output of said UV lamp detected by said second light detector occurring between a time step a) i) is performed and step a) ii) is performed, and between a time step b) i) is performed and step b) ii) is performed.

A further understanding of the functional and advantageous aspects of the invention can be realized by reference to the following detailed description and drawings.

BRIEF DESCRIPTION OF THE DRAWINGS

The invention will be more fully understood from the following detailed description thereof taken in connection with the accompanying drawings, which form a part of this application, and in which.

DETAILED DESCRIPTION OF THE PREFERRED EMBODIMENT

Figure 1:
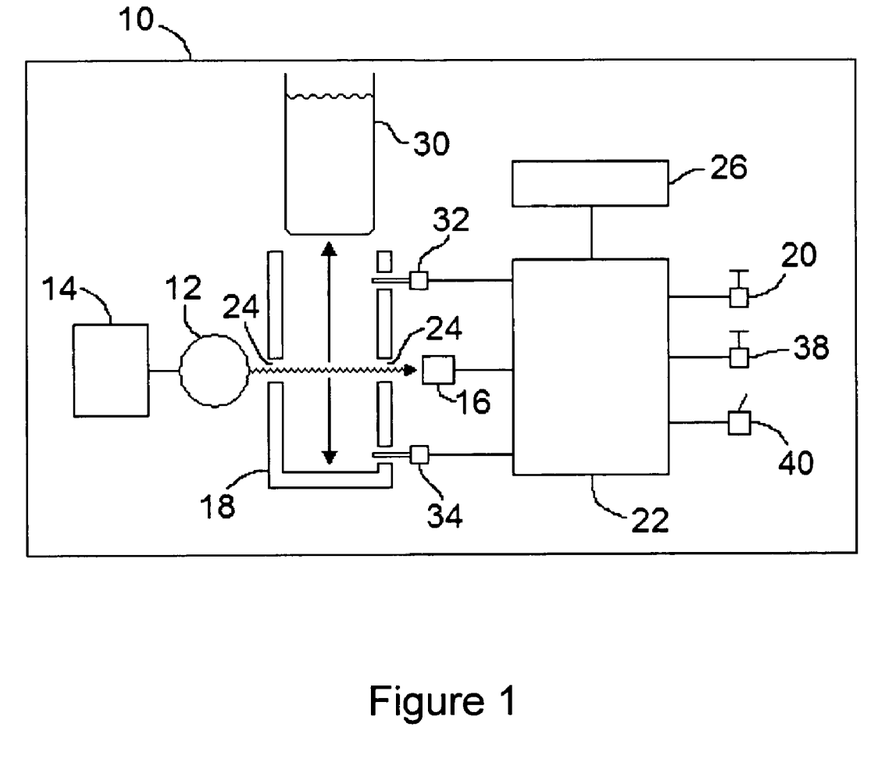
FIG. 1 is a block diagram showing a UV transmittance measuring device constructed in accordance with the present invention.

Referring to FIG. 1, a UV transmittance measuring device constructed in accordance with the present invention is shown generally at 10 and includes a single UV lamp 12 powered by a UV lamp ballast 14.

Lamp 12 can be any UV light source that emits light of a wavelength that can be absorbed by organic matter, generally between 250-290 nm range UV. Lamp 12 can be a mercury lamp, deuterium lamp or a deep UV LED light source. In a preferred embodiment, lamp 12 may be a mercury low pressure UV lamp emitting radiation with a wavelength of 254 nm as the UV source.

A sample vial holder 18 holds a sample vial 30 used to hold the liquid sample being tested. Sample vial holder 18 may be made of a material which is not degraded over time by exposure to UV light and for this reason a metal such as aluminum is preferred and if a metal is used apertures 24 are required on opposed faces of the sample vial holder 18 to provide a path for the UV light through the holder. Apertures 24 are not required if a material is used which is transparent to the UV wavelengths. It will be appreciated that the apertures 24 in the sample vial holder 18 could be formed such that they deliberately help to direct the UV light through the sample vial in a narrow beam for the purpose of reducing stray UV light. Also, a lens capable of transmitting UV light could be positioned in the UV light path between the UV lamp 12 and the sample vial holder 18 to focus the UV light into a narrow beam with a purpose of reducing stray UV light.

The sample vial 30 is made from a material that is transparent to UV light such as quartz but other materials may be used. The sample vial 30 is preferred to be square and have an inside width of 10 mm however any size and shape of vial can be used. The UV light must pass through the sample vial 30 on its way from the UV lamp 12 to a UV detector 16 located such that it detects any UV light transmitted through sample vial 30. A wider sample vial means the light must pass through more liquid and a narrower sample vial means the light must pass through less liquid. Wider sample vials can improve performance at higher UVT values yet decrease performance at lower UVT values. Narrower sample vials can improve performance at lower UVT values yet decrease performance at higher UVT values. If a wider or narrower sample vial is used the computation could compensate for the change in distance that the UV light must travel through the liquid such that the final UVT/UVA value displayed is relative to a 10 mm path through the sample liquid. This is preferred since the industry accepted UVT/UVA parameter assumes a 10 mm path length. This compensation requires only a simple multiplication.

A UV light detector 16 is mounted approximately halfway along the height of the vial holder 18 for measuring the intensity of UV light transmitted through the vial holder 18. The UV light detector 16 is sensitive to UV light in approximately the 200-400 nm range UV. UV light detector 16 may be made of any conventional radiation sensor material sensitive to UV light in the 200-400 nm range UV. In a preferred embodiment UV light detector 16 is a common commercially available SiC UV photodiode.

The two sensor mechanisms 32 and 34 provide the microprocessor 22 with the necessary information it requires to determine whether the UV light detector 16 is currently detecting the amount of UV light that is being transmitted through the sample vial 30 containing a liquid sample contained in the sample vial holder 18, or whether the UV light detector 16 is currently detecting the amount of UV light emitted directly from the UV lamp 12. The purpose of this configuration is to determine the change in lamp output between the time that the amount of UV light that penetrates through a liquid sample of known UV transmittance (or any other calibrator of known UV transmittance) is determined, and the time that the amount of UV light that penetrates through a liquid sample under test is determined.

In another embodiment of the device, sensor mechanisms 32 and 34 could instead be a program running on the microprocessor 22 which takes readings from the UV light detector 16 during the time that the user inserts the sample vial 30 into the sample vial holder 18. As the bottom of the sample vial 30 passes in front of the UV light detector 16 and apertures in the sample vial holder the UV light detector readings will drop, indicating to the microprocessor program that the sample vial 30 has been inserted into the vial holder 30.

The apparatus 10 is preferably configured to detect the amount of UV light emitted from the UV lamp 12 within a pre-selected period of time before the sensor mechanisms 32 and 34 sense the insertion of the sample vial 30, and detects the amount of UV light that passes through a liquid sample within a pre-selected quantity of time after the sensor mechanisms 32 and 34 detect the insertion of the sample vial. The purpose of this is to allow the determination of the amount of light emitted by the UV lamp 12 close to the same time that the amount of UV light that passes through the liquid sample contained in the sample vial 30 is determined.

The presence of the two sensor mechanisms 32 and 34 at the top and bottom of the sample vial holder 18 is to be able to separately detect the start and the finish of the sample vial 30 insertion into the sample vial holder 18 by the user. The purpose of detecting the start and the finish of the sample vial 30 insertion is to make sure that the microprocessor 22 does not take UV light detector readings from the UV light detector 16 during the sample vial 30 insertion. UV light detector readings taken during the sample vial 30 insertion would be inaccurate since the UV light detector readings would be affected both by inconsistencies in the sample vial 30 and by the base of the sample.

A sensor mechanism 32 is mounted near the top of the vial holder 18 and its function is to detect when the user starts insertion of the sample vial 30 into the vial holder 18. Sensor mechanism 32 can be any mechanism suitable for detecting the insertion of the sample vial 30 into the vial holder 18, including a microswitch or an IR led/detector. In a preferred embodiment sensor mechanism 32 is a low cost microswitch with a roller actuator.

A sensor mechanism 34 is mounted near the bottom of the vial holder 18 and its function is to detect when the user finishes insertion of the sample vial 30 into the vial holder 18. Sensor mechanism 34 can be any mechanism suitable for detecting the insertion of the sample vial 30 into the vial holder 18, including a microswitch or an IR led/detector. In a preferred embodiment sensor mechanism 34 is a low cost microswitch with roller actuator.

A microprocessor 22 is interfaced to UV light detector 16 and sensor mechanisms 32 and 34 and a visual display 26 is connected to the microprocessor 22. Visual display 26 can be any type of display capable of prompting the user to insert the sample vial 30 into the vial holder 18 at the appropriate times and indicating to the user the computed UVT/UVA of tested liquid samples, including LEDs, alphanumeric character LCDs and graphical LCDs. In the preferred embodiment visual display 26 is an alphanumeric character LCD.

Pushbuttons 20 and 38 are connected to microprocessor 22 which are operator activated. The role of pushbutton 20, when activated by the user is to alert the microprocessor 22 that the device is to begin the calibrate phase of operation. The role of pushbutton 38, when activated by the user is to alert the microprocessor 22 that the device is to begin the test phase of operation. Pushbuttons 20 and 38 can be standard pushbuttons or any other suitable indicator that can be user activated and send a signal to the microprocessor 22 when activated.

It will be appreciated that the device could be programmed to operate without the user activated pushbuttons 20 and 38, by programming the microprocessor in such a way that when the device is turned on the calibrate phase is automatically initiated and upon completion of the calibrate phase the test phase is automatically initiated.

Switch 40 is provided for converting the UVT calculated by the microprocessor 22 into units of UV absorbance (UVA), depending on the mode of operation desired by the operator.

Figure 2:
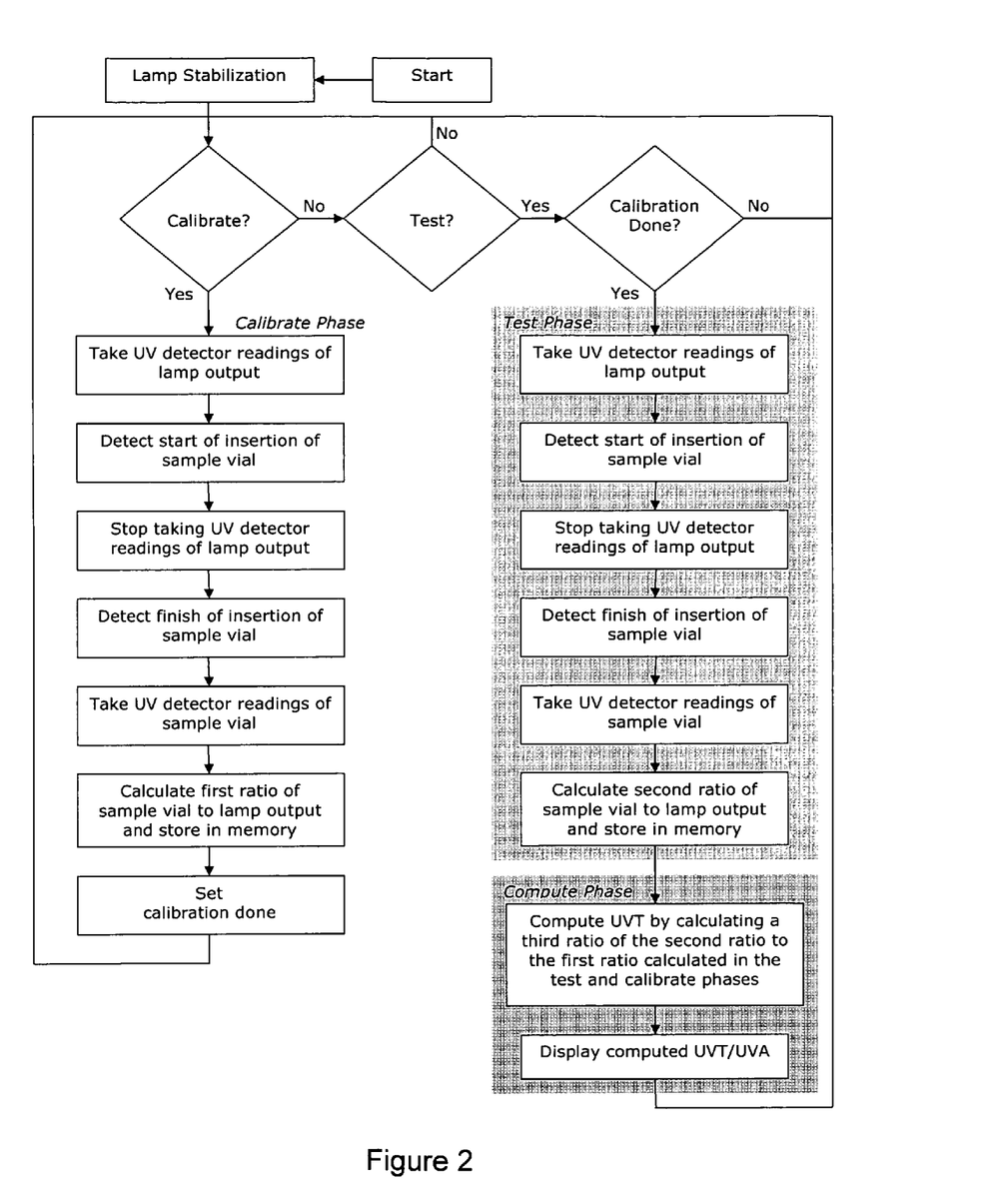
FIG. 2 is a flow diagram showing the steps undertaken by the device when calibrating and in operation.

FIG. 2 provides a flow chart giving the steps of both calibration and use of the device of FIG. 1 for measuring the UVT of a liquid sample.

In operation, the UV lamp 12 is allowed to reach a stable operating output characterized by a manageable amount of drift over time, as measured by the UV light detector 16. Microprocessor 22 is programmed to determine when the output of UV lamp 12 has become stable enough by measuring and comparing the UV lamp output at predetermined time intervals. Once certain stability parameters are met, the microprocessor 22 then sends electronic signals to the display 26 (preferably an alphanumeric character LCD) to tell the operator that the system is ready to be calibrated.

The industry accepted UVT parameter is defined as the ratio of the UV transmittance of a liquid sample under test (test sample) to the UV transmittance of a liquid sample of known transmittance (blank sample), preferably of 100% UVT. The UVA parameter can be calculated from the UVT parameter. The determination of the UV transmittance of the blank sample is often referred to as "zeroing" or "calibration". Instead of using a liquid sample of known UVT for calibration, the system may use a solid calibrator material with known UVT, to be used as a substitute for the liquid sample of known UVT.

Calibration must be performed before finding the UVT of the test sample. Button 20 is activated by the operator to indicate to the microprocessor 22 that the device is to begin the calibrate phase of operation. The UV light emitted from the UV lamp 12 shines towards UV light detector 16 after passing through the empty sample vial holder 18. At this time, the microprocessor 22 begins taking readings from the UV light detector 16. The microprocessor 22 signals the display 26 to communicate to the user to insert the sample vial 30 containing the blank sample into the vial holder 18.

The upper sensor mechanism 32 (preferably a microswitch) senses when the user starts insertion of the sample vial 30 containing the blank sample into the sample vial holder 18 and promptly signals the microprocessor 22. The microprocessor 22 stops taking readings from the UV light detector 16. The most recent readings taken from the UV light detector 16 are used by the microprocessor 22 to determine the UV light output from the UV lamp 12.

The lower sensor mechanism 34 (preferably a microswitch) senses when the user finishes insertion of the sample vial 30 into the sample vial holder 18 and promptly informs the microprocessor 22. The microprocessor 22 begins taking UV light detector readings from the UV light detector 16 for a specified time. The most recent readings taken from the UV light detector 16 are used by the microprocessor 22 to determine the amount of UV light able to pass through the sample vial 30 containing the blank sample.

The accuracy of UV light detector readings, whether they measure lamp output or the amount of light transmitted through the blank or test sample, can be improved by using signal conditioning electronics and/or by using various software averaging algorithms. In the preferred embodiment of the invention, signal conditioning electronics is used to improve UV light detector reading accuracy. Such signal conditioning electronics can generally include trans-impedance amplifiers, signal gain amplifiers, and various common analog to digital converters (ADCs).

Two sets of UV light detector readings are taken during the calibration procedure. Software running on microprocessor 22 is used to average the two sets of UV light detector readings to produce two final UV light detector readings $A_{cal}$ and $B_{cal}$. The first UV light detector reading $A_{cal}$ records the amount of UV light able to pass through the blank sample, and the second UV light detector reading $B_{cal}$ records the amount of light being output by the UV lamp 12 at that time. Note that the two UV light detector readings are taken within a few seconds of each other. If the delay between UV light detector reading $A_{cal}$ and $B_{cal}$ is too large, the UV lamp may have time to drift or fluctuate between the two UV light detector readings which would introduce errors into the UVT calculation. Note that UV light detector reading $B_{cal}$ can actually be taken either before the sample vial 30 is inserted or after the sample vial 30 is removed, as long as UV light detector reading $A_{cal}$ is taken while the sample vial 30 is inside the vial holder 18, and provided UV light detector reading $B_{cal}$ was taken a maximum of a few seconds before or after UV light detector reading $A_{cal}$. The preferred embodiment requires that UV light detector reading $B_{cal}$ is taken about 1 second before UV light detector reading $A_{cal}$ is taken, which provides enough time for the user to easily insert the sample vial 30 into the vial holder 18.

Microprocessor 22 calculates a first ratio of $A_{cal}$ divided by $B_{cal}$ which is then stored in memory for later use when calculating the UVT of a test sample. The user then removes the sample vial 30 containing the blank sample from the vial holder 18. This completes the calibrate phase of operation. Although unnecessary, calibration may be performed repeatedly at any time by the operator in order to verify the invention is operating in a correctly calibrated state.

After the device has been calibrated, the operator is able to start testing for the UVT of liquid samples.

As with the calibration procedure above, the test procedure first requires indicating to the microprocessor that a liquid sample is to be tested by means of a push button or other suitable indicator. More particularly, pushbutton 38 is pushed to indicate to the microprocessor 22 that the device is to begin the test phase of operation. The test procedure proceeds much the same as the calibration procedure as illustrated in FIG. 2, the only difference being that the user inserts the sample vial 30 containing the test sample, rather than the blank sample.

In summary, as in the calibration procedure, the test procedure produces two UV light detector readings. $A_{test}$ is the amount of UV light that passed through the test sample, and $B_{test}$ is the amount of UV light output by the UV lamp at that time. Microprocessor 22 calculates a second ratio of $A_{test}$ divided by $B_{test}$ which is then stored in memory for later use when calculating the UVT of a test sample. This completes the test phase of operation.

The next phase of operation is the compute phase. The microprocessor 22 is programmed to calculate the UVT of the test sample by taking a third ratio of the second ratio divided by the first ratio which were recorded during the previously completed calibrate and test phases of operation. More particularly, the UVT of the test sample is equal to the ratio recorded during the test phase divided by the ratio recorded during the calibrate phase. The result is the industry accepted UVT of the test sample. The following equation $E_1$ shows the basic calculation used to compute the UVT of the liquid sample under test:

$$E_1: UVT = \frac{A_{test}/B_{test}}{A_{cal}/B_{cal}}$$

where $A_{test}$ is the amount of UV light that passed through the test sample, $B_{test}$ is the amount of UV light output by the UV lamp during the test phase, $A_{cal}$ is the amount of UV light that passed through the blank sample, and $B_{cal}$ is the amount of UV light output by the UV lamp during calibration. Preferably, the microprocessor 22 program multiplies the result of equation $E_1$ by 100% to determine the UVT of the test sample. Note that the result of equation $E_1$ may need to be adjusted using a factory determined calibration curve or equivalent means to account for any offset errors or other errors introduced in the particular implementation of the design. Thus, the microprocessor 22 may include look-up tables or calibration curves, and may be programmed to correlate the calculated UVT ($E_1$) value to a UVT value that has been factory adjusted to compensate for any of the aforementioned offset errors or other errors.

The UVA of the test sample is easily calculated from the UVT determined above using a simple calculation of the inverse log. Note that the preferred embodiment of the invention includes a mechanism to select between two modes of operation. One mode allows the UVT to be displayed while the other mode allows the UVA to be displayed instead.

The microprocessor 22 then communicates with the display 26 to display the calculated UVT or UVA of the test sample.

At this point the microprocessor 22 waits for an input from pushbutton 20 or pushbutton 38 from the user, which will trigger the microprocessor 22 to enter either the calibrate or test phases of operation, respectively.

UV transmittance measuring device 10 may be configured to include a second UV light detector to measure the output of lamp 12 directly without the light passing through the sample vial holder 18. The purpose of the second UV light detector is to allow the microprocessor 22 to correct for changes in lamp output that occur between the times when the first UV light detector 16 is detecting the amount of UV light emitted from the UV lamp 12, and when the first UV light detector 16 is detecting the amount of UV light that passes through a liquid sample contained in the sample holder 18. Thus, the output from the second UV light detector representing the intensity of the UV lamp 12 allows the device to automatically correct for any lamp fluctuations that occur during this short interval.

Another way to reduce errors caused by changes in lamp output that occur between the times when the first UV light detector 16 is detecting the amount of UV light emitted from the UV lamp 12, and when the first UV light detector 16 is detecting the amount of UV light that passes through a liquid sample contained in the sample holder 18, is to use a software trending algorithm. Microprocessor 22 may use a software trending algorithm to allow the lamp output to be approximately predicted from previous readings from the UV light detector 16, in the attempt to predict and therefore correct for any changes in lamp output that occur during this short interval.

As used herein, the terms "comprises", "comprising", "including" and "includes" are to be construed as being inclusive and open ended, and not exclusive. Specifically, when used in this specification including claims, the terms "comprises", "comprising", "including" and "includes" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. An apparatus for measuring the transmittance of ultraviolet radiation through a liquid sample, comprising:
   a sample vial holder for holding a sample vial, the sample vial, holder defining a path therethrough for transmitting UV light through said sample vial holder;
   an ultraviolet lamp for emitting ultraviolet radiation positioned on one side of said sample vial holder for illuminating said sample vial holder;
   at least one sensor for sensing a presence or absence of said sample vial in said sample vial holder;
   a light detector located on the other side of said sample vial holder for detecting an intensity of ultraviolet radiation transmitted through said sample vial holder;
   a microprocessor connected to said ultraviolet lamp and said light detector and said at least one sensor, said microprocessor including processing means for processing ultraviolet light intensity signals received from said light detector, said microprocessor including processing means programmed for
   a) performing a calibration procedure by the steps of:
      i) measuring, for first specified period of time, ultraviolet light intensity of ultraviolet light emitted from the ultraviolet lamp without any sample vial located in said sample vial holder while said sensor is detecting the absence of said sample vial, and averaging said ultraviolet light intensity measurements over said first specified period of time to give a first ultraviolet light intensity,
      ii) measuring, for second specified period of time, ultraviolet light intensity of ultraviolet light transmitted through said sample vial when said sample vial is inserted into said sample vial holder so that a calibrator material located in said sample vial having a known ultraviolet transmittance is located in the path through said vial holder while said sensor is detecting the presence of said sample vial, and averaging said ultraviolet light intensity measurements over said second specified period of time to give a second ultraviolet light intensity, where said first and second ultraviolet light intensity measurements are taken within a maximum of a few seconds apart, and calculating a first ratio of the first and second ultraviolet light intensities,
      wherein said first and said second specified period of time can be different or the same;
   b) measuring ultraviolet light transmittance of a test liquid sample by the steps of:
      i) measuring for third specified period of time, ultraviolet light intensity of ultraviolet light emitted from the ultraviolet lamp without any sample vial located in said sample vial holder while said sensor is detecting the absence of said sample vial, and averaging said ultraviolet light intensity measurements over said third specified period of time to give a third ultraviolet light intensity,
      ii) measuring for fourth specified period of time, ultraviolet light intensity of ultraviolet light emitted from said sample vial upon insertion of said sample vial into said sample vial holder so that the test liquid sample being tested in a liquid quality measurement procedure is located in the path through said sample vial holder while said sensor is detecting the presence of said sample vial, and averaging said ultraviolet light intensity measurements over said fourth specified period of time to give a fourth ultraviolet light intensity, where said third and fourth ultraviolet light intensity measurements are taken within a maximum of a few seconds apart, and calculating a second ratio of the third and fourth ultraviolet light intensities, wherein said third and said fourth specified period of time can be different or the same; and c) calculating a third ratio of said first and second ratios to determine an ultraviolet transmittance (UVT) of the test liquid sample.

2. The apparatus according to claim 1 including a user activated first indicator means connected to said microprocessor for indicating to said microprocessor that said step a) calibration procedure is to be initiated, and including a user activated second indicator means connected to said microprocessor for indicating to said microprocessor that said step b) of measuring ultraviolet light transmittance of a test liquid sample is to be initiated.

3. The apparatus according to claim 1 wherein said microprocessor includes processing means for converting said ultraviolet transmittance (UVT) of the test liquid sample to ultraviolet absorbance of the test liquid sample.

4. The apparatus according to claim 1 wherein said sensor for sensing a presence or absence of said sample vial in said sample vial holder includes at least two sensors, a first sensor at a top of the sample vial holder for detecting the presence of the sample vial at a top of said vial holder and a second sensor at a bottom of the sample vial holder for detecting the presence of the sample vial at a bottom of the sample vial holder.

5. The apparatus according to claim 1 wherein said sensor for sensing a presence or absence of said sample vial in said sample vial holder is an infra-red emitter/detector device connected to said microprocessor.

6. The apparatus according to claim 1 wherein said sensor for sensing a presence or absence of said sample vial in said vial holder is a micro-switch connected to the microprocessor.

7. The apparatus according to claim 1 wherein said sensor for sensing a presence or absence of said sample vial in said vial holder is said light detector being monitored by said microprocessor for a decrease in light intensity occurring as said sample vial passes said apertures in each of said opposed side walls in said vial holder.

8. The apparatus according to claim 1 wherein said calibrator material is purified water having a calibration grade purity.

9. The apparatus according to claim 1 wherein said calibrator material is a solid having a known ultraviolet transmittance.

10. The apparatus according to claim 1 wherein said microprocessor includes a visual display for displaying transmittance and/or absorbance of said test sample.

11. The apparatus according to claim 10 wherein said visual display is an alpha numeric display.

12. The apparatus according to claim 1 wherein said sample vial holder is made of a material opaque to UV light, and includes apertures in opposed walls of said sample vial holder with said apertures being in registration with each other to define said path therethrough for transmitting UV light through said sample vial holder.

13. The apparatus according to claim 1 wherein said sample vial holder is made of a material substantially transparent in the ultraviolet such that UV light from the UV light source is transmitted through walls of said sample vial holder.

14. The apparatus according to claim 1 wherein said microprocessor is programmed to perform said step a) i) of said calibration procedure first then followed by step a) ii).

15. The apparatus according to claim 1 wherein said microprocessor is programmed to perform said step a) ii) of said calibration procedure a) first then followed by step a) i).

16. The apparatus according to claim 1 wherein said microprocessor is programmed to perform said step b) i) of said step of measuring ultraviolet light transmittance of the test liquid sample first and said step b) ii) of said measuring light transmittance of the test liquid sample second.

17. The apparatus according to claim 1 wherein said microprocessor is programmed to perform said step b) ii) of measuring ultraviolet light transmittance of the test liquid sample first and said step b) i) of said measuring light transmittance of the test liquid sample second.

18. The apparatus according to claim 1 wherein said microprocessor is programmed to monitor an output of said UV lamp and to determine when the output of the UV lamp will no longer vary its output by more than a pre-defined percentage of the output of the UV lamp.

19. The apparatus according to claim 1 wherein said microprocessor is programmed to wait a pre-determined length of time after said UV lamp is turned on to allow said UV lamp to stabilize before processing ultraviolet light intensity signals received from said light detector.

20. The apparatus according to claim 1 wherein said sample vial is made of quartz.

21. The apparatus according to claim 1 wherein said sample vial has a path length of about 10 mm.

22. The apparatus according to claim 1 wherein said sample vial has a path length of greater than or less than 10 mm.

23. The apparatus according to claims 1 wherein said microprocessor includes a look-up table or a calibration curve, and wherein said microprocessor is programmed to correlate the third ratio in said step c) to a UVT value that has been factory adjusted to compensate for any offset errors or other errors introduced in a particular implementation of said device.

24. The apparatus according to claim 1 wherein said microprocessor includes processing means for predicting an output light intensity of said UV lamp based on previous intensity signal readings from said light detector.

25. The apparatus according to claims 1 including a second light detector connected to said microprocessor for measuring a direct output of said UV lamp, and wherein said microprocessor is programmed to correct for fluctuations in the output of said UV lamp detected by said second light detector occurring between a time step a) i) is performed and step a) ii) is performed, and between a time step b) i) is performed and step b) ii) is performed.

26. The apparatus according to claims 1 wherein said microprocessor is programmed to prompt a user to insert said sample vial into said sample vial holder a pre-determined time after an initiation of step a) i), and a pre-determined time after an initiation of step b) i).

27. The apparatus according to claim 1 wherein said microprocessor is programmed to process said ultraviolet light intensity signals received directly from said light detector during step a) i) or b) I) for a pre-selected period of time prior to insertion of said sample vial, and wherein said microprocessor is programmed to process said ultraviolet light intensity signals received from said sample vial located in said sample vial holder during step a) ii) or b) ii) for a pre-selected period of time after insertion of said sample vial into said sample vial holder.

28. The apparatus according to claim 1 wherein said microprocessor is programmed to process said ultraviolet light intensity signals received directly from said light detector during step a) i) or b) i) for a pre-selected period of time after removal of said sample vial from said sample vial holder, and wherein said microprocessor is programmed to process said ultraviolet light intensity signals received from said sample vial located in said sample vial holder during step a) ii) or b) ii) for a pre-selected period of time prior to removal of said sample vial from said sample vial holder.

29. The apparatus according to claim 1 including a focusing lens capable of transmitting ultraviolet light positioned in the UV light path from said ultraviolet lamp to said light detector and between said ultraviolet lamp and said sample vial holder with a purpose of focusing the ultraviolet light path through the sample vial holder.

* * * * *

UNITED STATES PATENT AND TRADEMARK OFFICE
CERTIFICATE OF CORRECTION

PATENT NO.         : 7,462,835 B2                                              Page 1 of 1
APPLICATION NO.    : 11/455933
DATED              : December 9, 2008
INVENTOR(S)        : James Andrew Glover It is certified that error appears in the above-identified patent and that said Letters Patent is hereby corrected as shown below:

Title page item [73]
The name of the assignee of record should be listed as: 002134761 Ontario Ltd.

Signed and Sealed this

Seventeenth Day of March, 2009

JOHN DOLL
*Acting Director of the United States Patent and Trademark Office*